United States Patent [19]

Mattchen

[11] 4,106,181
[45] Aug. 15, 1978

[54] QUICK RELEASE MECHANISM FOR OSCILLATING SAW BLADE

[75] Inventor: Terry M. Mattchen, Van Nuys, Calif.

[73] Assignee: American Safety Equipment Corporation, Encino, Calif.

[21] Appl. No.: 712,730

[22] Filed: Aug. 9, 1976

[51] Int. Cl.$^2$ .................... B23P 11/02; A61B 17/14
[52] U.S. Cl. ................... 29/450 R; 29/446; 29/526; 30/216; 30/339; 83/698; 83/782; 128/317; 279/77; 403/374
[58] Field of Search ............... 128/317; 29/450, 446, 29/526; 403/373, 374; 83/835, 697, 698, 647, 782; 30/272 A, 339, 216; 279/77

[56] References Cited

U.S. PATENT DOCUMENTS

| | | | |
|---|---|---|---|
| 645,565 | 3/1900 | Manes | 279/77 |
| 1,493,372 | 5/1924 | Moon | 279/77 |
| 1,533,971 | 4/1925 | Castracane | 30/339 |
| 2,773,528 | 12/1956 | Gringer | 128/317 |
| 3,438,664 | 4/1969 | Meyer | 403/374 |
| 3,554,197 | 1/1971 | Dobbie | 128/317 |
| 3,977,289 | 8/1976 | Tuke | 83/698 X |
| 3,978,862 | 9/1976 | Morrison | 128/317 |

Primary Examiner—Othell M. Simpson
Assistant Examiner—W. D. Bray
Attorney, Agent, or Firm—Poms, Smith, Lande & Glenny

[57] ABSTRACT

One end of an oscillating saw blade has a notch, and spaced from the notch is a hole through the blade. The head of the tool has a slot having a shaft extending through the rear end of the slot for receiving the notch. A pin extends partially into the slot for receiving the hole. A closer in the form of a cam is cammed into and out of the slot for moving the hole on the blade onto the pin and moving the end of the blade having the hole and the notch against the bottom of the slot. The cam closer is locked in place to lock the blade in the slot. A handle is attached to the cam closer for manually rotating the cam, and the cam has an overcenter orientation where the resilient forces from the blade pushing on the cam tend to rotate the cam to a closed position. A stop is provided to intersect the handle and stop it in its locked position. A jaw of resilient material may be provided between the blade and the bottom of the slot to spread forces from the cam on the blade. The jaw is slightly curved so that camming tends to straighten the jaw, but the tendency for the jaw to resume its slightly curved orientation creates a force on the cam urging the cam to its overcenter position. The jaw also has a lip to prevent the blade from being inserted between the jaw and the cam. The jaw has an aperture through which the shaft passes, and the jaw slides along the shaft. A second aperture in the jaw mates with the pin to secure the jaw when the cam is holding the jaw against the blade.

19 Claims, 8 Drawing Figures

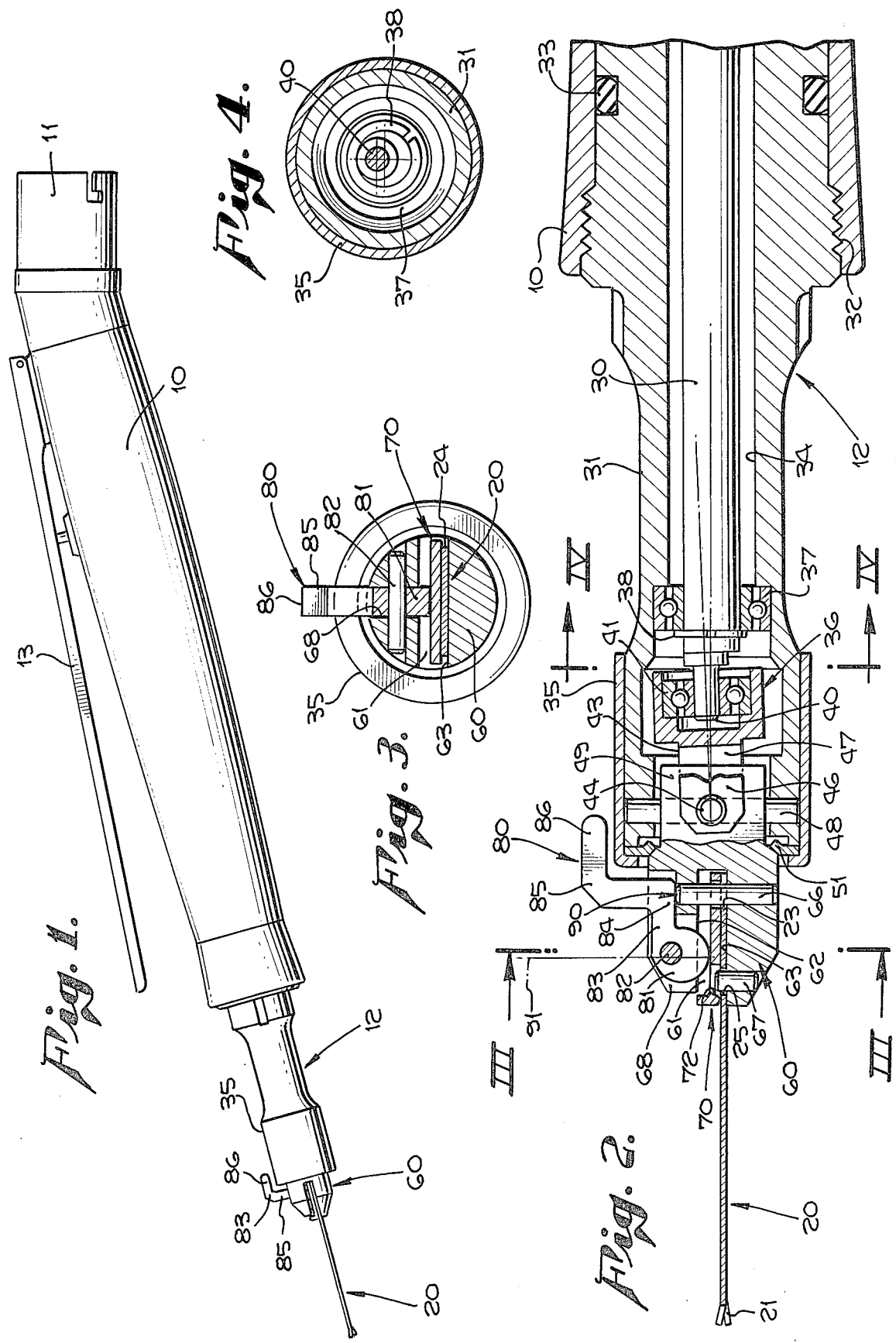

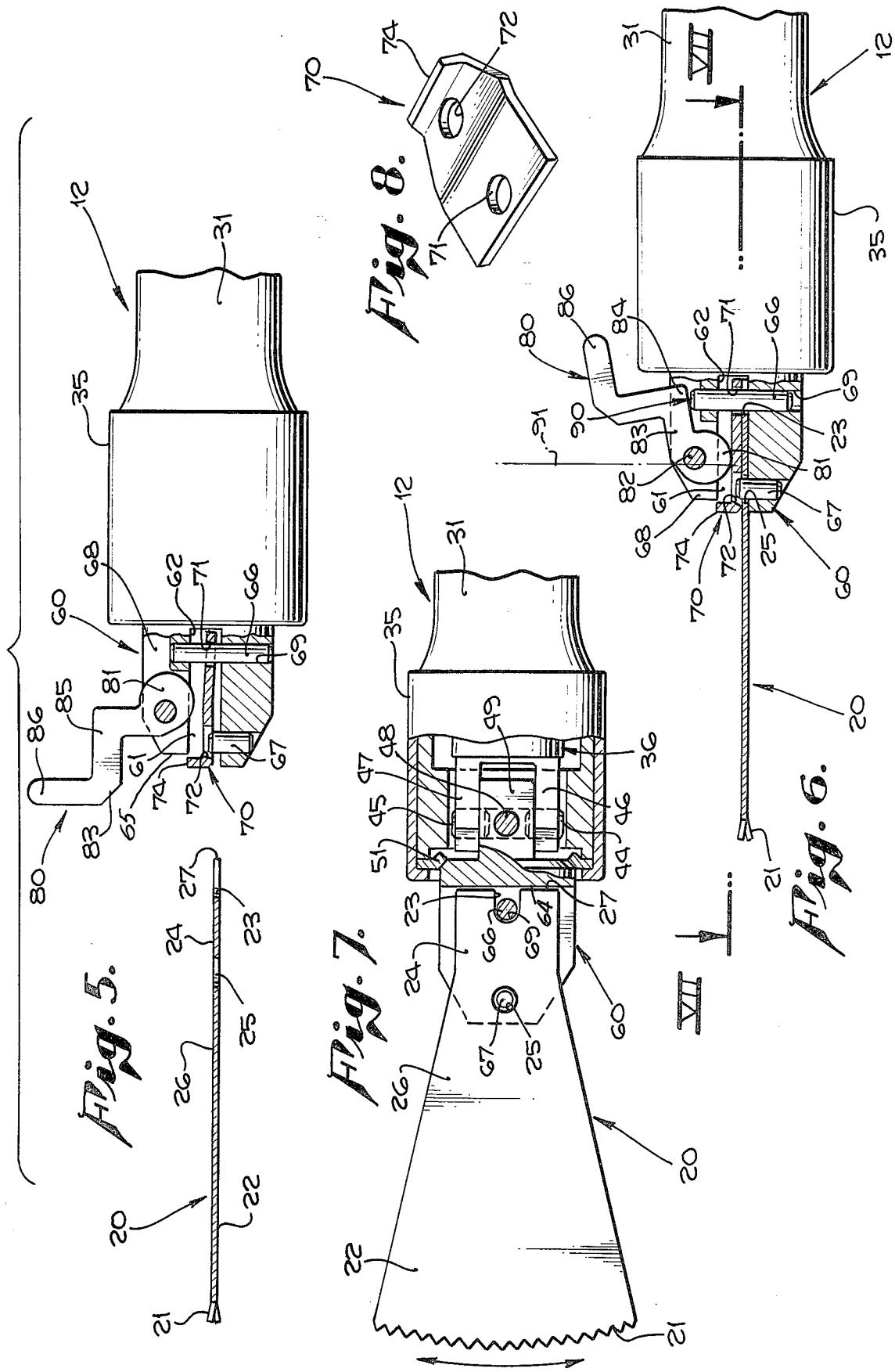

QUICK RELEASE MECHANISM FOR OSCILLATING SAW BLADE

BACKGROUND OF THE INVENTION

The present invention relates to a quick release mechanism to release and secure a blade in a surgical tool or other cutting device. The present invention has its greatest applicability in the surgical tool field. A need has developed for quickly releasing and attaching a blade to a surgical tool. The particular surgical tool that the invention has its greatest applicability is an oscillating saw. Typically, the saw oscillates at high frequency and has an elongated cutting blade having a cutting edge at one end of the blade. Because of the high frequencies and large forces developed, it is essential that the blade be secured in the tool. Typically, this has been done in a number of ways. One system utilizes a rotating chuck with jaws that are clamped as the chuck is rotated. These chucks have serious drawbacks, however. In order for the chuck to be tight enough to hold the blade, a chuck tightener or wrench must be used, but this adds an additional tool in the operating room which is undesirable. It is simple to lose chuck tighteners or wrenches, and one may be unavailable when the blade is to be changed.

Certain devices have attempted to replace the rotating chuck. For example, U.S. Pat. No. 3,943,934 to Bent uses a spring biased locking member locking a blade to latching pins received within an equal number of apertures. Such devices are excessively complex, and are difficult to maintain.

SUMMARY OF THE INVENTION

The principal objects of the present invention include disclosing and providing a quick release mechanism for securing and releasing a blade to an oscillating head and a method of releasing and locking a blade to the head of an oscillating saw. Another object of the present invention is to provide a quick release mechanism using few parts. Still another object of the present invention is to disclose and provide a quick release mechanism which can be adjusted to accomodate blades of different thicknesses. Still another object of the present invention is to provide a mechanism capable of quickly releasing and securing a blade in a surgical tool and also holding the blade securely in the tool. Other objects, advantages and novel features of the present invention will become apparent from the following detailed description of the invention when considered in conjunction with the accompanying drawings.

The quick release mechanism for securing and releasing a blade in an oscillating head includes a slot in the head for inserting the blade therein. The slot has a top and bottom. A shaft extends through the slot and includes means for preventing movement of the first portion of the blade in a plane parallel to the oscillations. A pin extends partially into the slot from the bottom thereof for preventing movement of the second portion of the blade in a plane parallel to the oscillations and permitting insertion and removal of the blade over the ends of the pin into the slot. A locking member movable into and out of the slot moves the blade against the bottom of the slot, and means are provided for mounting the locking member in the slot for locking an aperture in the blade over the pin. The device includes a cam which is cammed over the blade to lock the blade against the bottom of the slot. The cam has a handle for gripping by the surgeon or other user, and the tool has a stop for limiting the rotation of the cam to such a position that the forces exerted by the blade are overcenter on the cam to urge the handle against the stop and prevent rotating of the cam to the open condition.

A jaw member has a rear aperture so that it can slide on the shaft. The jaw also has a forward aperture aligned with a pin when the other aperture is over the shaft. The blade fits between the jaw and the bottom of the slot and the cam urges the jaw against the blade for distributing the forces from the cam. The jaw has a forward lip to align the jaw and to prevent the blade from being inserted between the jaw and the cam. The jaw also is slightly curved so that when it is urged against the blade and straightened by the cam, the restorative forces act on the cam to drive the cam to the overcenter condition.

BRIEF DESCRIPTION OF THE DRAWINGS

FIG. 1 is a side elevational view of the surgical tool utilizing the quick release mechanism of the present invention.

FIG. 2 is a sectional view of the forward end of the surgical tool showing in detail the quick release mechanism of the present invention.

FIG. 3 is a sectional view taken through plane III—III in FIG. 2.

FIG. 4 is a sectional view taken through plane IV—IV in FIG. 3.

FIG. 5 is a detail side elevational partially in section with the quick release mechanism in the open condition indicating minimal requirements for manual dexterity needed so that the blade can be inserted.

FIG. 6 is another side elevation, partially in section showing how to stop on the cam can be adjusted slightly to accommodate blades of different thicknesses.

FIG. 7 is a top view partially in section showing the detail of the quick release mechanism.

FIG. 8 is a perspective view of the jaw.

DETAILED DESCRIPTION OF THE PREFERRED EMBODIMENT

Prior to a detailed discussion of the quick release mechanism of the present invention, the operation of the surgical tool will be discussed. Referring to FIG. 1, there is shown a view of the surgical tool which has an elongated housing 10 which can be connected at the input end 11 to a source of air or other compressed gas. The other end of the tool is the output end 12, and it is to the output end that the blade 20 is mounted. Handle 13 is mounted on the housing 10 and controls the flow of air entering at the input end 11 of the surgical tool. The air entering the tool drives a vane motor which is connected to output shaft 30 which can be seen in FIG. 2. The vane motor, gas control and connection to the source of air or other gas is disclosed in detail in my copending application, Ser. No. 712,729 filed Aug. 9, 1976 and the disclosure therein is incorporated herein by reference.

Conversion of Rotation to Oscillation. The output end 12 of the housing includes an output housing 31 which is assembled to the housing 10 by means of threads 32. O-ring 33 seals the output end of the tool. The output shaft 30 is mounted within a bore 34 extending axially through output housing 31 and is connected to the rotor motor to rotate therewith. Although it is possible to provide interchangeability with the oscillating system of the present invention and other rotating tools, the present invention is designed primarily to be an oscillating saw. Therefore, the means for converting the rotation to oscillation are permanently attached to the surgical tool.

Means for converting rotation of the shaft to oscillating motion, shown generally at 36 is mounted in the forward end 35 of the output housing. Output shaft 30 rotates in bearing race 37, which is held within the output housing 31 by snap ring 38. Eccentric shaft 40 is mounted eccentrically on output shaft 30, and the eccentric shaft is mounted for rotation between bearings 41. It should be noted that the eccentric shaft is also mounted at an angle to the axis of output shaft 30, and as output shaft 30 rotates, eccentric shaft 40 travels a conical path.

Yoke 43 is mounted to horizontal pins 44, 45 in forward end 35 of the output housing. It should be noted that the axis of eccentric shaft 40 passes through the center of the axis extending through horizontal pins 44, 45. In FIG. 7, the two arms 46 and 47 of yoke 43 support horizontal pins 44 and 45 of the horizontal pin. A vertical pin 48 is also mounted in forward end 35 of the output housing, and is perpendicular to horizontal pins 44, 45. Block 49, a part of head 60, is mounted for pivoting with respect to vertical pin 48. The axis of rotation of eccentric shaft 40 also passes through vertical pin 48.

As shaft 30 rotates causing rotation of the eccentric shaft 40, the yoke moves in a conical path. The vertical components of the motion causes pivoting of arms 46 and 47 about pins 44 and 45. The horizontal component of the motion causes oscillation of the yoke about vertical pin 48. The horizontal components of motion are transmitted to the head 60 which oscillates about pin 48.

The Quick Release Mechanism. The quick release mechanism for securing and releasing blade 20 to oscillating head 60 includes slot means in the head for inserting the blade therein, the slot having top and bottom walls. Referring to the exemplary embodiment, particularly FIGS. 2, 5 and 6, head 60 includes a slot 61 having a top wall 62 and a bottom wall 63. Blade 20 is inserted in the slot. Shaft means 66 extends through slot means 61 and associated therewith are means for preventing movement of a first portion of the blade in a plane parallel to the oscillations. The means for preventing movement of the portion of the blade include a notch at one end portion of the blade. Referring to FIG. 7 in the exemplary embodiment, blade 20 has a cutting edge 21 at the edge of a first portion 22 of blade 20 and a notch 23 at the end of a second portion 24 of the blade. Notch 23 is received against shaft 66 when blade 20 is inserted in slot 61 to prevent movement of second portion 24 of the blade adjacent notch 23 relative to the head in a plane parallel to the oscillations. The intersection of notch 23 with shaft 66 prevents movement of the rear or second portion 24 of blade 20 in a direction parallel to the oscillations.

Blade 20 also includes a hole 25 through the blade between cutting edge 21 and notch 23, and hole 25 is located in the central portion 26 of blade 20. Pin means 67 extends partially into slot means 61 from bottom wall 63 for preventing movement of the central portion 26 of blade 20 in a plane parallel to the oscillations. Pin 67 receives hole 25 when notch 23 is against shaft 66 for preventing movement of the portion of the blade 26 adjacent the hole relative to the head in a plane parallel to the oscillations. The shaft and pin cooperate to prevent movement of the entire blade relative to the head in a direction parallel with the oscillations. Referring again to FIG. 7 in the preferred exemplary embodiment, shaft 66 and pin 67 are the same distance from each other as is notch 23 from hole 25. Shaft 66 and pin 67 are located along the center line of head 60, and notch 23 and hole 25 are also located along the center line of blade 20. This prevents unbalanced forces from acting on the blade during oscillation thereof.

In the preferred embodiment, especially as shown in FIG. 7, when notch 23 is against shaft 66 and hole 25 is over pin 67, the back wall 27 of blade 20 abuts end wall 64 of slot 61. This provides additional support for the blade. Because the blade is secured at two points (notch 23 and hole 25), movement of the blade in a plane parallel to the oscillations is prevented. The abutment of rear face 27 of the blade to the end wall 64 of slot 61 adds to the prevention of movement in that plane.

As stated above, pin means 67 extends only partially into slot 61 from bottom wall 63 so that blade 20 can be inserted and removed over the end of pin means 67 into and out of slot means 61. Referring to FIG. 5 in the exemplary embodiment, it should first be explained that jaw means which is indicated generally at 70 and which has a function which will be described hereinbelow, is mounted in slot means 61 and has an aperture 71 for movement along shaft means 66. Therefore, the jaw means 70 is movable up and down in slot means 61. In the exemplary embodiment shown in FIG. 5, jaw means can be raised higher than it is shown to permit insertion of the blade between the bottom of jaw 70 and the top of pin 67. When notch 23 is abutting shaft 66, hole 25 will be over pin 67.

Closing means are movable into the slot means for moving the blade against the bottom wall of the slot means and for moving the central portion of the blade onto the pin means to prevent movement of the blade relative to the head. Turning again to the exemplary embodiment in FIG. 2, closing means 80 in the form of cam 81 is movable into and out of the slot for moving second portion 24 of blade 20 downward against bottom wall 63 of slot 61 so that hole 25 moves onto pin means 67. The closing means prevents movement of the blade perpendicular to the oscillations. Means for mounting the cam means for rotation on the head for camming the blade against the bottom of the slot are also provided. As best seen in FIGS. 2 and 3, such means in the exemplary embodiment include a horizontal pin 82 mounted in head 60. Pin 82 extends through vertical opening 68 in which is mounted cam 81 which is journaled for rotation on horizontal pin 82. As cam means 81 is rotated from the FIG. 5 position to the FIG. 2 position, it extends into slot means 61 to cam blade 20 against the bottom of the slot 63.

Locking means on the closing means locks the closing means in the slot to lock the blade in the slot. The locking means comprises stop means on the head for stopping rotation of the cam means to prevent rotation of the cam means beyond a certain point. The stop means is mounted such that when the stop means intersects the cam means, the line of force on the cam means is directed to one side of the axis of rotation of the cam means to urge the cam means against the stop means.

Referring to FIG. 2 in the exemplary embodiment, cam means 81 does not actually contact blade 20 because jaw 70 is interposed therebetween. Although the invention could be used without the jaw, the jaw is useful to spread the force from the cam on second portion 24 of blade 20 and to perform other functions. The camming will be discussed with reference to the interposed jaw 70.

When cam 81 is rotated about horizontal pin 82, a portion of the cam face extends into the slot and moves jaw 70 against blade 20 and pushes the blade against the bottom wall 63 of slot 61. With reference to FIG. 2, cam means 81 includes handle means 83. In order to lock the cam means in place, handle means 83 is rotated from the orientation in FIG. 5 to the orientation in FIG. 2.

A first extension of the handle means in the exemplary embodiment abuts stop means 90, which in the exemplary embodiment is the upper end of shaft 66. When handle 83 is rotated to the FIG. 2 orientation and first extension 84 is contacting the stop means 90, the cam is designed to be in a overcenter condition. That is, cam 81 is cammed tightly against jaw 70, blade 20 and the bottom wall 63 of the slot means 61. There is some resiliency in the system as the metal parts are compressed or subjected to shear stresses. Therefore, the jaw will exert a force upward on the cam. The cam is designed and mounted such that the force is directed to the left (FIG. 2) of horizontal pin 82, for example along line 91. The force exerted by the jaw against the cam tends to rotate the cam in the clockwise direction and urges the handle against stop means 90.

As this locking means is an important feature, it is desirable to maximize the force from the jaw acting on the cam 91 so that handle 83 is urged against stop means 90. However, it would be difficult to close the locking means if only compressive and shearing forces were relied upon to produce forces on the cam. Therefore, the jaw means performs a second function of having spring means thereon for biasing the cam means against the stop means in the overcenter condition. Although slightly exaggerated in the drawings, jaw 70 (FIG. 8) has a slight curvature that can also be seen in FIG. 5. When the cam 81 is rotated into slot 61 against the curved jaw 70, cam 81 tends to depress the curved portion and flatten it against the blade. It takes less force to rotate cam 81 to flatten jaw 70 than it would to rotate the cam against compressive and shear forces to attain a tight fit. The forces tending to restore jaw 70 to its slightly bent condition are sufficient to urge the cam against the stop in the overcenter reaction.

It should be recognized that it would be possible to accomplish the same result with a slightly curved second portion 24 of blade 20, but the jaw 70 of the present invention allows the use of flat blades.

The jaw also has a forward aperture 72 which fits over pin means 67. When the cam means is in the locked condition, the jaw is prevented from moving in a plane parallel to the oscillations by shaft 66 and pin 67 in a manner similar to that which shaft 66 and pin 67 secure blade 20.

Lip means on the jaw extend upward away from the bottom of the slot and extend outside of the head for directing the blade between the jaw and the bottom of the slot when the blade is inserted in the slot to prevent the blade from being inserted between the cam and the jaw. Referring to FIG. 5 in the preferred exemplary embodiment, lip 74 is at the forward end of jaw 70 and extends upward bearly out of slot 61. The lip directs the blade between the jaw and the bottom wall 63 of the slot when the blade is inserted in the slot. When the forward aperture 72 of the jaw is not engaged by pin 67, lip 74 abuts forward wall 65 of head 60 to prevent jaw 70 from pivoting about shaft 66 at aperture 72. Back wall 73 of the jaw also interacts with end all 64 of the slot to correctly position the jaw.

It is possible that if a thicker blade were used, the cam could no be rotated to the stop means 90. Therefore, means for mounting the stop means for movement on the head to change position that the cam means contacts the stop means are provided to change the locked orientation of the cam means. In the exemplary embodiment, shaft 66 is mounted in bore 69 in the head, and the shaft can be moved axially in the bore to adjust the position that stop means 90 contacts first extension 84 of handle means 83. The view shown in FIG. 6 of the exemplary embodiment is somewhat exaggerated. Shaft 66 could be threaded in bore 69 for adjustability. A press fit is also acceptable.

Handle 83 is designed to be substantially accommodated within vertical opening 68. First extension 84 of handle 83 extends horizontally at 86 along the vertical opening, and vertical extension 85 of handle 83 extends upward along the edge of output housing 31. The second horizontal extension extends along the top of forward end 35 of output housing 31. It can be seen in FIG. 1 that handle 83 does not interfere with the use of the tool. However, it is easy to pivot the handle counterclockwise to rotate the cam out of the slot so that the blade can be removed. The handle can then be rotated back to the FIG. 1 orientation when a blade is inserted in the slot.

The method of locking the blade to the head of the oscillating saw includes inserting blade 20 into slot 61 on head 60. Notched portion 23 of the blade is fitted against shaft 66 at the rear of the slot. Hole 25 in the blade is located on pin 67 extending into the slot. The blade is cammed against the bottom of the slot by cam 81 whereby the blade is held against the bottom of the slot and against the shaft and the pin. The cam 81 is driven to an overcenter condition to lock the cam in its camming position holding the blade against the bottom of the slot.

Thus, a quick release mechanism for securing and releasing a blade to an oscillating head has been disclosed which meets the aforementioned objects and other objects apparent herein. It will be understood that various modifications and changes may be made in the configuration described above which may come within the spirit of this invention, and all such changes and modifications coming within the scope of the appended claims are embraced thereby.

I claim:

1. In an oscillating head having a quick release mechanism for securing and releasing a blade to the oscillating head, and including slot means in the head for inserting the blade therein, the slot means having top and bottom walls, shaft means extending through the slot means for preventing movement of a rear portion of the blade adjacent the shaft means in a plane parallel to the oscillations, the blade having means for cooperating with the shaft means, pin means extending partially into the slot means from the bottom wall thereof for preventing movement of a central portion of the blade in the plane coincident to the oscillations and permitting insertion and removal of the blade over the end of the pin means into and out of the slot means, cam means and means for mounting the cam means for rotation in the slot means for camming the blade against the bottom wall of the slot means and for moving the central portion of the blade onto the pin means to prevent movement of the blade relative to the head, and locking means for locking the cam means in the location holding the blade to the bottom of the slot means and on the pin means, the improvement comprising the provision of the locking means comprising:

stop means on the head for stopping rotation of the cam means to prevent rotation of the cam means beyond a certain point, and means for mounting the stop means such that when the stop means intersects the cam means, the line of force on the cam means is directed to one side of the axis of rotation of the cam means to urge the cam means against the stop means.

2. The improvement of claim 1 further comprising jaw means mounted in the slot means and having an aperture therethrough for movement along the shaft means for placement over the blade when the blade is inserted in the slot means for distributing forces from the cam means on the blade.

3. The improvement of claim 2 further comprising spring means mounted in the slot means for biasing the cam means against the stop means when the force from the jaw means is directed to one side of the axis of rotation of the cam means.

4. The improvement of claim 3 wherein the spring means is defined by the jaw means.

5. The improvement of claim 3 further comprising lip means on the jaw means extending upward away from the bottom of the slot means and extending outside of the head for directing the blade between the jaw and the bottom of the slot means when the blade is inserted in the slot means to prevent the blade from being inserted between the cam means and the jaw means.

6. In an oscillating surgical tool having a head, a quick release mechanism on the head, for releasing and securing a blade to the head, the blade having a cutting edge at the end of a first portion thereof, a notch at the end of a second portion of the blade and a hole through the blade between the cutting edge and the notch, slot means extending through the head for receiving therein the end of the blade having the notch, the slot having top and bottom walls, shaft means extending through the head for receiving the notch thereagainst to prevent movement of the end of the second portion of the blade adjacent the notch relative to the head in a plane coincident with the oscillations, pin means extending partially into the slot means for receiving the hole when the notch is against the shaft for preventing movement of the portion of the blade adjacent the hole relative to the head in a plane parallel to the oscillations, the shaft and pin cooperating to prevent movement of the blade relative to the head in a direction coincident with the oscillations, cam means and means for mounting the cam means for rotation on the head for rotation from out of the slot means into the slot means for camming the hole of the blade onto the pin means and for camming the second portion of the blade against the bottom of the slot for preventing movement of the blade perpendicular to the oscillations, and locking means for locking the closing means in the slot means to lock the blade in the slot means, the improvement comprising the provision of:

the locking means comprising stop means on the head for stopping rotation of the cam means to prevent rotation of the cam means beyond a certain point and means for mounting the stop means such that when the stop means intersects the cam means, the line of force on the cam means is directed to one side of the axis of rotation of the cam means to urge the cam means against the stop means.

7. The improvement of claim 6 further comprising the provision of the cam means comprising handle means attached to the cam means for rotating the cam means, and means for mounting the stop means for stopping rotation of the cam means beyond the certain point where the line of force on the cam is directed to the side of the axis of rotation of the cam means to urge the handle means against the stop means.

8. The improvement of claim 6 further comprising jaw means mounted in the slot means and having an aperture therethrough for movement along the shaft means for placement over the blade when the blade is inserted in the slot means for distributing forces from the cam means on the blade.

9. The improvement of claim 8 further comprising spring means mounted in the slot means for biasing the cam means against the stop means when the force from the jaw means is directed to one side of the axis of rotation of the cam means.

10. The improvement of claim 9 further comprising lip means on the jaw means extending upward away from the bottom of the slot means and extending outside of the head for directing the blade between the jaw and the bottom ofthe slot means when the blade is inserted in the slot means to prevent the blade from being inserted between the cam means and the jaw means.

11. The improvement of claim 10 further comprising a second opening on the jaw means for receiving the pin means therein to prevent movement of the jaw means in a plane parallel to the oscillations.

12. The improvement of claim 9 further comprising a second opening on the jaw means for receiving the pin means therein to prevent movement of the jaw means in a plane parallel to the oscillations.

13. The improvement of claim 6 further comprising means for mounting the stop means for movement on the head to change the position that the cam contacts the stop means to change the locked orientation of the cam means for accommodating different blade thicknesses.

14. The improvement of claim 13 further comprising means for mounting the shaft means for adjustable movement in the head, one end of the shaft means comprising the stop means.

15. In an oscillating head having a quick release mechanism for securing and releasing a blade to the oscillating head, and including slot means in the head for inserting the blade therein, the slot having top and bottom walls, shaft means extending through the slot means for preventing movement of a rear portion of the blade adjacent the shaft means in a plane coincident to the oscillations, the blade having means cooperating with the shaft means, pin means extending partially into the slot means from the bottom wall thereof for preventing movement of a central portion of the blade in the plane coincident to the oscillations and permitting insertion and removal of the blade over the end of the pin means into and out of the slot means, camming means movable into the slot means for camming the blade against the bottom wall of the slot means and for moving the central portion of the blade onto the pin means to prevent movement of the blade relative to the head, and locking means on the head for locking the camming means in the location holding the blade to the bottom of the slot means and on the pin means, the improvement comprising the provision of:

jaw means mounted on the slot means and having an aperture therethrough for movement along the shaft means for placement over the blade when the blade is inserted in the slot means for distributing forces from the camming means on the blade.

16. The oscillating head of claim 15 wherein the camming means has a securing position locking the blade and a releasing position releasing the blade, the improvement further comprising spring means in the slot means for biasing the camming means to the securing position.

17. The oscillating head of claim 16 wherein the spring means is defined by the jaw means.

18. The improvement of claim 15 further comprising lip means on the jaw means extending upward away from the bottom of the slot means and extending outside of the head for directing the blade between the jaw and the bottom of the slot means when the blade is inserted in the slot means to prevent the blade from being inserted between the camming means and the jaw means.

19. A method of locking a blade to a head of an oscillating saw comprising mounting a resilient jaw in a slot on the head with a hole in the jaw about a shaft at the rear of the slot, inserting the blade into the slot on the head, fitting a notched portion of the blade against the shaft at the rear of the slot, locating a hole in the blade on a pin extending into the slot, and camming a cam to the jaw against the blade and the blade against the bottom of the slot whereby the blade is held against the bottom of the slot and against the shaft and the pin, driving the cam to an overcenter condition to lock the cam in its camming position holding the blade against the bottom of the slot and urging the cam to its overcenter condition.

* * * * *

UNITED STATES PATENT AND TRADEMARK OFFICE
CERTIFICATE OF CORRECTION

PATENT NO. : 4,106,181
DATED : Aug. 15, 1978
INVENTOR(S) : Terry M. Mattchen

It is certified that error appears in the above—identified patent and that said Letters Patent are hereby corrected as shown below:

Column 1, line 43, change "accomodate" to --accommodate--.
Column 2, line 35, change "to" to --the--. Column 6, line 4, change "no" to --not--. Column 8 (within claim 13), line 39, after "cam" and before "contacts" add --means--. Column 10, line 2, change "camming" to --closing--.

*Signed and Sealed this*

*Twenty-seventh* Day of *March 1979*

[SEAL]

Attest:

RUTH C. MASON
*Attesting Officer*

DONALD W. BANNER
*Commissioner of Patents and Trademarks*